United States Patent [19]

Behr

[11] Patent Number: 5,011,983
[45] Date of Patent: Apr. 30, 1991

[54] PREPARATION AND REACTIONS OF OMEGA-HALOSULFONYL PERFLUOROALKANESULFONATES

[75] Inventor: Fred E. Behr, Maplewood, Minn.

[73] Assignee: Minnesota Mining and Manufacturing Company, St. Paul, Minn.

[21] Appl. No.: 6,110

[22] Filed: Jan. 23, 1987

[51] Int. Cl.$^5$ .................................. C07C 303/00
[52] U.S. Cl. ...................... 562/113; 562/41
[58] Field of Search ............. 260/513 F, 513 R; 562/41, 113

[56] References Cited

U.S. PATENT DOCUMENTS

| | | | |
|---|---|---|---|
| 2,732,398 | 1/1956 | Brice et al. | 260/513 F |
| 2,951,051 | 10/1960 | Tiers . | |
| 2,965,659 | 4/1961 | Tiers . | |
| 3,346,612 | 10/1967 | Hansen | 260/456 |
| 4,329,478 | 5/1982 | Behr . | |
| 4,386,214 | 5/1983 | Behr . | |
| 4,423,197 | 12/1983 | Behr . | |
| 4,610,829 | 9/1986 | Lalu | 260/513 R |

OTHER PUBLICATIONS

Cahn, A. and Lynn, J. L., Jr., *Kirk-Othmer Encyclopedia of Chemical Technology*, 3rd Ed., 22, pp. 332-432 (John Wiley & Sons 1983).
Knaggs, E. A. Nussbaum, M. L., Schultz, A., *Kirk-Othmer Encyclopedia of Chemical Technology*, 3rd Ed., 22, pp. 1-45 (John Wiley & Sons 1983).
X. Cleary, J. Organ. Chem., 45, 2727-2729 (1980).
R. D. Howells and J. D. McCown, *Chem Reviews*, 77, 69-92 (1977).
G. V. D. Tiers, *J. Org. Chem.*, 28, 1244-1246 (1963).

*Primary Examiner*—Alan Siegel
*Attorney, Agent, or Firm*—Gary L. Griswold; Walter N. Kirn; Eloise J. Maki

[57] ABSTRACT

Omega-chlorosulfonyl perfluoroalkanesulfonates and omega-fluorosulfonyl perfluoroalkane sulfonates. These compounds can be used to prepare esters, amides, or latent catalysts for the polymerization of cationically-sensitive monomers. The ω-chlorosulfonyl perfluoroalkanesulfonates can be reacted with ethylenically unsaturated compounds to incorporate hydrophilic perfluoroalkanesulfonate groups into the ethylenically unsaturated compound.

11 Claims, No Drawings

PREPARATION AND REACTIONS OF OMEGA-HALOSULFONYL PERFLUOROALKANESULFONATES

FIELD OF THE INVENTION

This invention relates to perfluoroalkane-sulfonates and their derivatives.

DESCRIPTION OF RELATED ART

The reactions of sodium fluoride, aluminum chloride, and zinc chloride with perfluoroalkanesulfonic acid anhydrides of the type $(R_fSO_2)_2O$ have been described by G. V. D. Tiers, *J. Org. Chem.*, 28, 1244–1246 (1963) and reviewed by R. D. Howells and J. D. McCown, *Chem. Reviews*, 77, 69–92 (1977). Tiers also converted perfluorinated sulfonyl fluorides to the corresponding chlorides by reaction with $PCl_5 \cdot 2ZnCl_2$. Tiers observed that direct reaction of the anhydride with potassium chloride gave little or no yield of sulfonyl chloride.

Organomagnesium bromides, chlorides, and iodides have been reacted with trifluoromethanesulfonic acid anhydride to produce a variety of mixed products, X. Creary, *J. Org. Chem.*, 45, 2727–2729 (1980).

Perfluorooctanesulfonyl chloride has been reacted with terminally ethylenically unsaturated aliphatic acids in the presence of organic peroxides, as shown in U.S. Pat. No. 2,951,051. Perfluorooctanesulfonyl chloride has also been reacted with certain ethylenically unsaturated aliphatic compounds in the presence of ultraviolet light or organic peroxides, as shown in U.S. Pat. No. 2,965,659. In both the '051 and '659 patents fluoroaliphatic groups were added to a double bond of an olefin, yielding a product with enhanced water repellency.

The present inventor's U.S. Pat. Nos. 4,329,478, 4,386,214 and 4,423,197 describe cyclic perfluoroaliphaticdisulfonic acid anhydrides, their sulfonamide derivatives and their use as catalysts for the cure of cationically-sensitive monomers.

SUMMARY OF THE INVENTION

The present invention provides novel ω-chlorosulfonyl and ω-fluorosulfonyl perfluoroalkanesulfonate compounds. For brevity, these compounds will sometimes be referred to herein as "ω-sulfonylsulfonates". Unlike the sulfonyl fluorides and chlorides described by Tiers, supra, the ω-sulfonylsulfonates can, if desired, be obtained in excellent yields from potassium chloride. Preferably the ω-sulfonylsulfonates have the formula:

$$XSO_2R_fSO_3M \qquad \text{I}$$

In the above Formula I, $R_f$ is a divalent perfluoroalkylene radical containing two to five backbone (i.e., catenary) carbon atoms, or a divalent perfluorocycloalkylene radical containing four to seven, and preferably six, ring atoms. $R_f$ is optionally substituted by one or more straight chain, branched, or cyclic perfluoroalkyl groups of one to twelve (preferably one to four) carbon atoms. $R_f$ preferably has a total of up to 14 carbon atoms. Preferably $R_f$ has the formula $-(CF_2)_m-$ wherein m is two to four. $R_f$ can contain non-adjacent heteroatoms such as O or N atoms. X is Cl or F. M is a salt-forming cation, preferably K, Rb, Cs, or $NR_4$ wherein each R is independently selected from H and lower (e.g., $C_1$ to $C_4$) alkyl groups.

The ω-sulfonylsulfonates can, using the procedure described in more detail below, be prepared in high yield and with excellent purity.

This invention also provides adducts with vicinal chloro and perfluoroalkyl sulfonate groups that can be prepared by reacting an ω-chlorosulfonyl perfluoralkanesulfonate (an "ω-chlorosulfonylsulfonate") with an ethylenically unsaturated compound (e.g., an olefin). A chlorine atom and the group $-R_fSO_3M$ will add to sites of ethylenic unsaturation, forming an adduct with vicinal chloro and $R_fSO_3M$ groups (e.g., as depicted in Formula II below) and releasing sulfur dioxide. For brevity, these vicinal chloro, perfluoroalkylsulfonate adducts will sometimes be referred to herein as "olefin adducts". Preferred olefin adducts contain one or more groups of the formula:

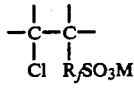

II wherein $R_f$ and M are as defined above and the remaining valences of the carbon atoms shown in Formula II are satisfied by atoms such as H, Cl or F, or groups such as alkyl, cycloalkyl, aryl, or combinations thereof (e.g., aralkyl or fluoroalkyl). The carbon atoms shown in Formula II can individually or together be part of one or more cyclic groups or can be a part of a polymeric backbone or polymer side chain group. Accordingly, the olefin adduct of Formula II can be a repeating unit in a polymer containing many $-Cl$ and $-R_fSO_3M$ moieties.

DETAILED DESCRIPTION

The ω-sulfonylsulfonates of the invention are conveniently prepared from the cyclic perfluoroaliphatic disulfonic acid anhydrides of U.S. Pat. No. 4,329,478. The acid anhydride is added to an anhydrous solution of a chloride or fluoride of the desired cation M, dissolved in an appropriate aprotic solvent, e.g., acetonitrile or methylene chloride. The solvent should not be subject to polymerization by the acid anhydride. Insoluble metal halides (e.g., NaF, $AlF_3$, $ZnF_2$, or $PCl_2$, or $PCl_5 \cdot 2ZnCl_2$) should be reacted neat rather than in solvent, using the procedures described by Tiers, cited above. In general, purer products are obtained using a solvent. Preferred chlorides or fluorides of the desired cation M include KCl, KF, RbCl, RbF, CsCl, CsF, $AlCl_3$, $ZnCl_2$, $NH_4Cl$, $NH_4F$, and $(n-C_4H_9)_4HCl$.

The reactants are stirred at a temperature between ambient and reflux (e.g., 20 to 120° C.) for a time sufficient to cause complete reaction (e.g., 0.5 to 8 hours). The reaction time will depend in part upon the reactivity of both the acid anhydride and the chloride or fluoride. It is sometimes desirable to add additional aprotic solvent to moderate the reaction temperature. The product usually forms a waxy or crystalline solid that can be recovered by diluting the reaction mixture with a non-polar solvent (e.g., methylene chloride), and removing the product by filtration. Depending on the particular product, the desired degree of purity, and the available equipment, the product can also be recovered by removing the solvent(s) by distillation or evaporation, or by cooling and filtering the reaction mixture.

The above reaction can be illustrated schematically as follows:

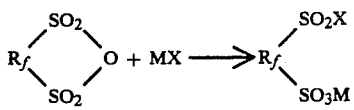

($R_f$, M and X are as defined above).

Representative ω-sulfonylsulfonates of the invention are shown below in Table I.

TABLE I

| Compound No. | ω-Sulfonylsulfonates Formula |
|---|---|
| 1 | $KO_3S(CF_2)_2SO_2Cl$ |
| 2 | $KO_3S(CF_2)_2SO_2F$ |
| 3 | $KO_3S(CF_2)_3SO_2Cl$ |
| 4 | $KO_3S(CF_2)_3SO_2F$ |
| 5 | $RbO_3S(CF_2)_3SO_2Cl$ |
| 6 | $CsO_3S(CF_2)_3SO_2F$ |
| 7 | $NH_4O_3S(CF_2)_3SO_2F$ |
| 8 | $KO_3S(CF_2)_4SO_2Cl$ |
| 9 | $KO_3S(CF_2)_4SO_2F$ |
| 10 | $KO_3SCF_2C(CF_3)_2CF_2SO_2F$ |
| 11 | $KO_3S\text{-cyclo-}C_6F_{10}SO_2F$ |

The ω-sulfonylsulfonates have particular utility as chemical intermediates. For example, they can be used to prepare esters, e.g., by reaction with a phenol to form a product with excellent thermal and hydrolytic stability, and having utility as an ion exchange resin, or a strong acid catalyst (e.g., for esterification reactions). The ω-sulfonylsulfonates can be reacted with polymers having amine functionality to prepare modified polyamides having pendant hydrophilic sulfonic acid groups. The ω-sulfonylsulfonates also can be reacted with ammonia or an amine to form latent catalysts for polymerization of cationically-sensitive monomers. The ω-chlorosulfonylsulfonates can be added to the double bond(s) of an ethylenically unsaturated (e.g., olefinic) compound under free-radical conditions to yield an olefin adduct containing one or more groups of Formula II. This reaction is particularly useful and can be illustrated schematically as follows:

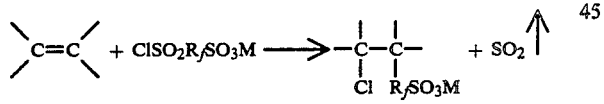

($R_f$ and M are as defined above).

Preferably, the ω-chlorosulfonylsulfonate $ClSO_2R_fSO_3M$ is added to a solution of the desired ethylenically unsaturated compound in a suitable polar aprotic solvent, e.g., acetonitrile. The ω-chlorosulfonylsulfonate can be employed in stoichiometric equality, deficiency or excess, dependent upon the ease of reaction and upon the characteristics (e.g, the level of residua-1 unsaturation) desired in the olefin adduct. The resulting heterogeneous mixture is stirred at a suitable temperature, e.g, 20°-100° C., under irradiation with UV light, e.g., a low wattage wide spectrum source such as a sunlamp. The reaction should be allowed to continue until the desired extent of reaction occurs. Stoichiometric addition of ω-chlorosulfonylsulfonates to carbon-carbon double bonds ordinarily can be accomplished in about 0.5 to 8 hours, with completion of the reaction generally coinciding with cessation of the evolution of $SO_2$ gas from the reaction mixture.

The product olefin adduct can, depending upon its solubility characteristics, be isolated by removal of solvent, or by other convenient methods of chemical recovery and purification.

The olefin adduct contains oleophobic $R_f$ groups with hydrophilic —$SO_3M$ tails. Thus, the present invention provides a convenient means for incorporating hydrophilic fluorochemical groups into appropriately reactive substances, thereby modifying surface properties.

As an alternative to UV irradiation, an organic peroxide such as benzoyl peroxide can be used to form the olefin adduct, in which case the temperature of reaction typically should be at or above the decomposition temperature of the peroxide, e.g., 60° to 120° C.

Examples of ethylenically unsaturated compounds that can be used to prepare the olefin adduct include vinylidene fluoride, perfluoropropylene, crotonic acid, maleic anhydride, itaconic acid, 1-octene, hendecenoic acid, polybutadiene, unsaturated polyesters (e.g., from reaction between maleic anhydride and a glycol), and the like. Other suitable olefins are cited in U.S. Pat. Nos. 2,951,051 and 2,965,659 or will be familiar to those skilled in the art.

Representative olefin adducts of the invention are shown below in Table II:

TABLE II

| Adduct No. | Olefin Adducts Formula |
|---|---|
| 1 | $ClCH_2(CF_2)_4SO_3K$ |
| 2 | $KO_3S(CF_2)_4CFClCF_3$ |
| 3 | $KO_3S(CF_2)_3CH_2CHCl(CH_2)_5CH_3$ |
| 4 | $H_4NO_3S(CF_2)_3CH_2CHCl(CH_2)_5CH_3$ |
| 5 | $KO_3S(CF_2)_3CH_2CHCl(CH_2)_8COOH$ |
| 6 | $KO_3S(CF_2)_4CH_2CHCl(CH_2)_8COOH$ |
| 7 | $H_4NO_3S(CF_2)_2CH_2CHCl(CH_2)_9CH_3$ |
| 8 | $\text{HOOCCH}_2\text{CClCOOH}$<br>\|<br>$CH_2(CF_2)_3SO_3K$ |
| 9 | (structure with F-substituted cyclohexane, Cl and $(CF_2)_3SO_3K$ substituents) |
| 10 | $\leftarrow O(CH_2)_4OCOCH_2CClCO\rightarrow_n$<br>\|<br>$CH_2(CF_2)_3SO_3K$ |

Dehydrochlorination of an olefin adduct containing vicinal chlorine and hydrogen atoms, followed by hydrogenation, can be carried out, if desired, to yield saturated, chlorine-free perfluoroalkanesulfonates. The reaction can be illustrated schematically as follows:

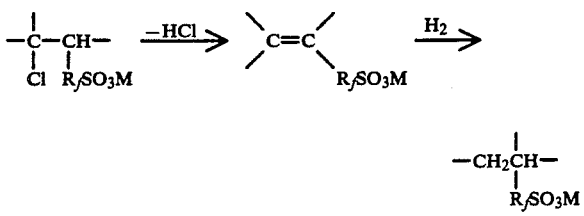

($R_f$ and M are as defined above).

Reaction of an ω-sulfonylsulfonate of Formula I with an amine or ammonia yields a sulfonamide. If M in Formula I is an ammonium cation, the sulfonamide is of the type shown in U.S. Pat. No. 4,329,478. If M is a metal cation, then the sulfonamide is believed to be novel. The reaction can be illustrated schematically as follows:

$$XSO_2R_fSO_3M + RNH_2 \rightarrow RHNSO_2R_fSO_3M + HX$$

($R_f$, X, M and R are as defined above).

As shown in U.S. Pat. No. 4,329,478, sulfonamides where M is an ammonium or organoammonium cation have utility as latent catalysts for the polymerization of cationically-sensitive monomers, e.g., epoxy resins. Olefin adducts of Formula II in which M is an ammonium or organoammonium cation can likewise be used as such latent catalysts.

The objects and advantages of this invention are further illustrated in the following examples. Unless otherwise indicated all parts and percentages are by weight.

EXAMPLE 1

This example describes the preparation of potassium 2-chlorosulfonyl-1,1,2,2-tetrafluoroethane-sulfonate (Compound No. 1, Table I).

A glass reaction vessel was heated to 130° C. and assembled while hot to minimize water absorption. Tetrafluoro-1,2-ethanedisulfonic acid anhydride (2.76 parts) was added to a slurried mixture of anhydrous potassium chloride (1.0 parts) in anhydrous acetonitrile (7.8 parts). An exothermic reaction ensued. The resulting heterogeneous mixture was stirred at ambient temperature (about 25° C.) for 20 hours and then heated to 40° C. for 1 hour. Excess potassium chloride was removed by filtration. The filtrate was concentrated using reduced pressure to yield a waxy solid. The solid was dissolved in acetonitrile (about 8 parts) and mixed with decolorizing carbon to remove a colored impurity. The decolorized solution was filtered through diatomaceous earth and diluted with methylene chloride (about 16 parts). The product (2.4 parts, calculated yield 67%) was obtained by crystallization from the solvent mixture. The product was soluble in water and could be recrystallized from water, indicating good hydrolytic stability. The infrared (IR) spectrum of the product exhibited major absorptions at 1414 cm$^{-1}$ ($SO_2Cl$), 1280 and 1260 cm$^{-1}$ (CF) and 1040 cm$^{-1}$ ($SO_3^{31}$). The Fluorine Nuclear Magnetic Resonance ($^{19}$FNMR) spectrum for the product exhibited major absorptions at $-112$ ppm ($CF_2SO_3^-$) and $-101$ ppm ($CF_2SO_2Cl$). This spectral data was consistent with the structure $KO_3SCF_2CF_2SO_2Cl$. A portion of the product was dissolved in acetonitrile and converted to the sulfonamide derivative $KO_3SCF_2CF_2SO_2NH_2$, a pale yellow solid, by bubbling anhydrous ammonia into the solution, filtering off the $NH_4Cl$ that precipitated and removing the solvent.

EXAMPLE 2

This example describes the preparation of potassium 2-fluorosulfonyl-1,1,2,2-tetrafluoroethanesulfonate (Compound No. 2, Table I).

Tetrafluoro-1,2-ethanedisulfonic acid anhydride (0.68 parts) was added to a slurried suspension of anhydrous potassium fluoride (0.475 parts) in anhydrous acetonitrile (7.8 parts). An immediate exothermic reaction ensued. The mixture was stirred at ambient temperature for 1 hour, heated to 40° C. for 1 hour, cooled and the excess potassium fluoride removed by filtration. The solvent was removed using reduced pressure to yield a solid whose IR spectrum exhibited major absorptions at 1455 cm$^{-1}$ ($SO_2F$), 1290 and 1260 cm$^{-1}$ (CF) and 1045 cm$^{-1}$ ($SO_3^-$). The $^{19}$FNMR spectrum exhibited major absorptions at $+45$ ppm ($SO_2F$), $-105$ ppm ($CF_2SO_2F$) and $-113$ ppm ($CF_2SO_3^-$). This spectral data was consistent with the structure $FSO_2CF_2CF_2SO_3K$.

EXAMPLE 3

This example describes the preparation of potassium 3-chlorosulfonyl-1,1,2,2,3,3-hexafluoropropane sulfonate (Compound No. 3, Table I).

Hexafluoro-1,3-propanedisulfonic acid anhydride (5 parts) was added rapidly to a heterogeneous mixture of anhydrous potassium chloride (2.66 parts) and anhydrous acetonitrile (20 parts). The temperature of the reaction mixture increased to 30° C. when the acid anhydride was added. The mixture was heated at reflux temperature for 2 hours. Crystallization of the product occurred as the mixture was cooled. The resulting lustrous white crystals were filtered and the crystals were washed with methylene chloride to yield 6.2 parts $KO_3SO(CF_2)_3SO_2Cl$ as evidenced by IR and $^{19}$FNMR analysis (1415 cm$^{-1}$ ($SO_2Cl$); 1280 and 1260 cm$^{-1}$ (CF); and 1060 cm$^{-1}$ ($SO_3^-$); $-114$ ppm $\phi$ )$CF_2SO_3^-$); $-117$ ppm $\phi$ (center $CF_2$); and $-102$ ppm $\phi$ ($CF_2SO_2Cl$)). The calculated product yield was 99%.

EXAMPLE 4

This example describes the preparation of potassium 3-fluorosulfonyl-1,1,2,2,3,3-hexafluoropropane sulfonate (Compound No. 4, Table I).

Hexafluoro-1,3-propanedisulfonic acid anhydride (1 part) was added to a slurried mixture of anhydrous potassium fluoride (0.40 parts) and anhydrous acetonitrile (7.8 parts). An exothermic reaction ensued along with rapid formation of solids. The resulting heterogeneous reaction mixture was stirred overnight at ambient temperature. The following day the mixture was heated to 40° C. for 1 hour, diluted with methylene chloride and filtered. The filtrate was concentrated at reduced pressure to yield 1.3 parts crude product. An analytical sample was prepared by recrystallization from a 1:2 (by volume) acetonitrile:methylene chloride solvent mixture. Spectral analysis by IR and $^{19}$FNMR (1455 cm$^{-1}$ ($SO_2F$); 1265 cm$^{-1}$ (CF, broad); and 1065 cm$^{-1}$ ($SO_3^-$); $-114$ ppm $\phi$ ($CF_2SO_3^-$); $-118$ ppm $\phi$ (center $CF_2$); $-106$ ppm $\phi$ ($CF_2SO_2$); and $+45$ ppm $\phi$ ($SO_2F$)), and elemental analysis (calculated: C 10.2, F 37.8, S 18.2; Found: C 10.0, F 37.5, S 18.6) indicated that the desired product $KO_3S(CF_2)_3SO_2F$ had been obtained.

EXAMPLE 5

This example describes the preparation of rubidium 3-chlorosulfonyl-1,1,2,2,3,3-hexafluoropropane sulfonate (Compound No. 5, Table I).

Hexafluoro-1,3-propanedisulfonic acid anhydride (1 part) was quickly added to a rapidly stirred suspension of anhydrous rubidium chloride (0.73 parts) in anhydrous acetonitrile (16 parts). An exothermic reaction ensued with accompanying formation of a solid product. The mixture was heated to 70° C. for 30 minutes, cooled and the solid removed by filtration and dried. 1.4 Parts of a white crystalline product were obtained. The IR spectrum of the product was consistent with the structure $RbO_3S(CF_2)_3SO_2Cl$ (1414 cm$^{-1}$ ($SO_2Cl$); 1271 cm$^{-1}$ (CF, broad); and 1059 cm$^{-1}$ ($SO_3^-$)).

EXAMPLE 6

This example describes the preparation of cesium 3-fluorosulfonyl-1,1,2,2,3,3-hexafluoropropane sulfonate (Compound No. 6, Table I).

Hexafluoro-1,3-propanedisulfonic acid anhydride (1 part) was added to a stirred mixture of anhydrous cesium fluoride (0.46 parts) and anhydrous acetonitrile (7.8 parts). An immediate exothermic reaction ensued. The temperature of the reaction mixture rose to 27° C. and an increase in turbidity of the mixture was noted. The mixture was heated at reflux temperature for 30 minutes, resulting in the formation of additional solids. The 5 mixture was cooled, filtered and dried to yield 1.4 parts of a white crystalline product. The IR spectrum of the product was consistent with the structure $CsO_3S(CF_2)_3SO_2F$ (1456 cm$^{-1}$ ($SO_2F$); 1265 cm$^{-1}$ (CF, broad); and 1045 cm$^{-1}$ ($SO_3^-$)).

EXAMPLE 7

This example describes the preparation of ammonium 3-fluorosulfonyl-1,1,2,2,3,3-hexafluoropropane sulfonate (Compound No. 7, Table I).

Hexafluoro-1,3-propanedisulfonic acid anhydride (1.0 part) was added to a stirred solution of anhydrous ammonium fluoride (0.11 parts) and anhydrous acetonitrile (9.4 parts). The resulting homogeneous reaction mixture was heated at 70° C. for 30 minutes, cooled to ambient temperature and the solvent removed using reduced pressure to yield a hygroscopic white solid. The IR spectrum of the product was consistent with the structure $H_4NO_3S(CF_2)_3SO_2F$ (1456 cm$^{-1}$ ($SO_2F$); 1265 cm$^{-1}$ (CF, broad); 1046 cm$^{-1}$ ($SO_3^-$); and 3223 and 1659 cm$^{-1}$ ($NH_4^+$)).

A portion of the product was dissolved in anhydrous acetonitrile and reacted with excess anhydrous ammonia to yield the known sulfonamide derivative $NH_4O_3S(CF_2)_3SO_2NH_2$. 0.1 Parts of the sulfonamide were dissolved in γ-butyrolactone (0.9 parts), and 0.1 parts of the resulting catalyst solution were added to 0.9 parts 3,4-epoxycyclohexylmethyl-3,4-epoxycyclohexanecarboxylate ("ERL 4221" epoxide). The resulting clear solution was allowed to stand at ambient temperature 30 hours with no noticeable increase in viscosity. A thin coating was applied to a clean metal plate using a glass rod coating bar. The plate was placed in an oven at 130° C. for 10 minutes. A clear, hard coating resulted.

EXAMPLE 8

This example describes the preparation of potassium 4-chlorosulfonyl-1,1,2,2,3,3,4,4-octafluorobutanesulfonate (Compound No. 8, Table I).

Octafluoro-1,4-butanedisulfonic acid anhydride (0.25 parts) was added to a stirred mixture of anhydrous potassium chloride (0.26 parts) and anhydrous acetonitrile (3.9 parts). The mixture was stirred at ambient temperature for 30 minutes, heated at reflux temperature for 30 minutes, then cooled to ambient temperature, filtered, and the filtrate concentrated using reduced pressure to yield a solid product whose IR spectrum was consistent with the structure $ClSO_2(CF_2)_4SO_3K$ (1415 cm$^{-1}$ ($SO_2Cl$); 1280, 1260 and 1240 cm$^{-1}$ (CF); and 1052 cm$^{-1}$ ($SO_3^-$)).

EXAMPLE 9

This example describes the preparation of potassium 4-fluorosulfonyl-1,1,2,2,3,3,4,4-octafluoro-butanesulfonate (Compound No. 9, Table I).

Following the procedure of Example 8, octafluoro1,4-butanedisulfonic acid anhydride (0.20 parts) was reacted with anhydrous potassium fluoride (0.20 parts) in acetonitrile (3.9 parts). The pale yellow solid product contained some inorganic salt impurities (believed to be $KF \cdot SO_2$) which were removed by dissolving the solids in acetonitrile, filtering the remaining solids from the solution and removing the solvent from the filtrate using reduced pressure. The IR spectrum of the product was consistent with the structure $FSO_2(CF_2)_4SO_3K$ (1455 cm$^{-1}$ ($SO_2F$); 1280 and 1240 cm$^{-1}$ (CF); and 1050 cm$^{-1}$ ($SO_3^-$)).

EXAMPLE 10

This example describes the preparation of the olefin adduct potassium 1,1,2,2,3,3-hexafluoro-5-chlorohendecanesulfonate (Adduct No. 3, Table II).

A mixture of $KO_3S(CF_2)_3SO_2Cl$ (from Example 3, 0.3 parts), anhydrous acetonitrile (15.7 parts) and 1-octene (0.183 parts) was stirred for 4 hours under ultraviolet light irradiation at 50°-60° C. Although the ω-chlorosulfonylsulfonate was only partly soluble at the beginning of the photolysis, complete dissolution of the solids was evident at the end of the reaction. The solvent was removed using reduced pressure to yield a solid product. The IR and NMR spectra of the product were consistent with the structure $KO_3S(CF_2)_3CH_2CHCl(CH_2)_5CH_3$ (2940 and 2920 cm$^{-1}$ (CH); 1260-1240 cm$^{-1}$ (CF, broad); 4.2 ppm δ (($CH_2$)$_5$, multiplet); 2.7 ppm δ ($CF_2CH_2$); −112 ppm φ ($CF_2CH_2$); −124 ppm φ (center $\overline{CF_2}$); −114 ppm φ ($O_3S\underline{CF_2}$); $J_{HF}$=19 Hz).

EXAMPLE 11

This example describes the preparation of the olefin adduct potassium 1,1,2,2,3,3-hexafluoro-5-chloro-13-carboxytridecanesulfonate (Adduct No. 5, Table II).

A mixture of $KO_3S(CF_2)_3SO_2Cl$ (from Example 2, 0.10 parts), anhydrous acetonitrile (1.6 parts) and ω-hendecenoic acid (0.048 parts) was irradiated with a sunlamp for 4 hours, during which time the mixture became homogeneous. The solvent was removed under a dry nitrogen gas stream to yield a white solid product. The IR spectrum of the product was consistent with the structure $KO_3S(CF_2)_3CH_2CHCl(CH_2)_8COOH$ (2920 and 2850 cm$^{-1}$ (CH): 1705 cm$^{-1}$ (C=O); 1260 cm$^{-1}$ (CF, broad); and 1080 cm$^{-1}$ ($SO_3^-$)). The absorption band at 1625-1615 cm$^{-1}$ (C=C) was present in the starting olefin but absent in the product.

EXAMPLE 12

This example describes the preparation of the olefin adduct ammonium 1,1,2,2,3,3-hexafluoro-5-chlorohendecanesulfonate (Adduct No. 4, Table II) and its utility as a latent catalyst for epoxy resin polymerization.

Potassium 1,1,2,2,3,3-hexafluoro-5-chlorohendecanesulfonate (from Example 10, 1 part) was added to sufficient aqueous ethanol to dissolve all solids, then converted from the potassium salt to the corresponding acid using an ion exchange column containing the acid form of "Amberlite IRA-120" resin. The eluate, containing $HO_3S(CF_2)_3CH_2CHCl(CH_2)_5CH_3$, as treated with 15M $NH_4OH$ to increase the pH to 8. The resulting aqueous solution was concentrated on a steam bath to yield a white crystalline product which was dried in a vacuum oven. The IR spectrum of the product was consistent with the structure $H_4NO_3S(CF_2)_3CH_2CHCl(CH_2)_5CH_3$ (2932 and 2959 cm$^{-1}$ (CH); 1250 cm$^{-1}$ (CF, broad); 1084 cm$^{-1}$ (SO$_3^-$); and 3224 and 1429 cm$^{-1}$ (NH$_4^+$)).

A catalytic amount of this ammonium salt (0.01 parts) was added to ERL 4221 epoxide (1.0 part) and the resulting mixture gently warmed at 40° C until the ammonium salt dissolved. The mixture was allowed to remain at ambient temperature for 24 hours with no apparent increase in viscosity. Upon heating the mixture to 130° C. for 10 minutes an amber, brittle polymeric solid was formed.

In another experiment, a stock catalyst solution was prepared by dissolving 1 part of the ammonium salt in 10 parts γ-butyrolactone. A portion of this catalyst solution (0.1 parts) was added to ERL 4221 epoxide (1.0 part). The resulting homogeneous liquid was placed in an oven at 130° C. for 15 minutes. The epoxy liquid increased in viscosity, and upon cooling to ambient temperature, a clear, slightly yellow, hard brittle polymer formed.

Various modifications and alterations of this invention will become apparent to those skilled in the art without departing from the scope and spirit of this invention. It should be understood that this invention is not to be limited to the illustrative embodiments set forth herein.

I claim:

1. Fluorinated, omega-chlorosulfonyl perfluoroalkanesulfonate and omega-fluorosulfonyl perfluoroalkanesulfonate compounds having the formula:

XSO$_2$R$_f$SO$_3$M wherein R$_f$ is a divalent perfluoroalkylene radical containing two to five backbone carbon atoms or a divalent perfluorocycloalkylene radical containing four to seven ring atoms, R$_f$ is optionally substituted by one or more straight chain, branched, or cyclic perfluoroalkyl groups of one to twelve carbon atoms, X is Cl o F, and M is a salt-forming cation.

2. Compounds according to claim 1, wherein R$_f$ has the formula —(CF$_2$)$_m$— wherein m is two to four.

3. Compounds according to claim 1, wherein X is Cl.

4. Compounds according to claim 1, wherein X is P.

5. Compounds according to claim 1, wherein M is K, Rb or Cs.

6. Compounds according to claim 1, wherein M is NR$_4$ wherein each R is independently selected from H and lower alkyl groups.

7. The compound ClSO$_2$(CF$_2$)$_3$SO$_3$K according to claim 2.

8. Vicinal chloro, perfluoroalkanesulfonate adducts containing one or more groups of the formula:

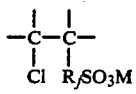

wherein R$_f$ is a divalent perfluoroalkylene radical containing two to five backbone carbon atoms or a divalent perfluorocycloalkylene radical containing four to seven ring atoms, M is a salt-forming cation and the remaining valences of said groups are satisfied by H, Cl or F atoms, or alkyl, cycloalkyl, or aryl groups, or combinations thereof.

9. Adducts according to claim 8, wherein a plurality of said groups are present in said adduct and said groups are part of a polymeric backbone or polymer side chain group.

10. Adducts according to claim 8, wherein M is K, Rb or Cs.

11. The adduct KO$_3$S(CF$_2$)$_3$CH$_2$CHCl(CH$_2$)$_5$CH$_3$ according to claim 8.

* * * * *

UNITED STATES PATENT AND TRADEMARK OFFICE
CERTIFICATE OF CORRECTION

PATENT NO. : 5,011,983
DATED : April 30, 1991
INVENTOR(S) : FRED E. BEHR It is certified that error appears in the above-identified patent and that said Letters Patent is hereby corrected as shown below:

Col. 2, line 45, delete "or $PCl_2$,".
Col. 2, line 51, "$(n-C_4H_9)_4HCl$" should be --$(n-C_4H_9)_4NCl$--.
Col. 3, line 57, "residua-1" should be --residual--.
Col. 5, line 45, "$(SO_3^{31})$." should be --$(SO_3^-)$.--.
Col. 6, line 21-22, "$KO_3SO(CF_2)_3SO_2Cl$" should be --$KO_3S(CF_2)_3SO_2Cl$--.
Col. 10, line 1, "Cl o F," should be --Cl or F,--.
Col. 10, line 6, "P" should be --F--.
Col. 10, line 13, "claim 2." should be --claim 1.--.

Signed and Sealed this

Tenth Day of November, 1992

Attest:

DOUGLAS B. COMER

*Attesting Officer*   *Acting Commissioner of Patents and Trademarks*